(12) United States Patent
Lamb, Jr.

(10) Patent No.: US 7,078,034 B2
(45) Date of Patent: Jul. 18, 2006

(54) IN VITRO ACTIVATED γ δ LYMPHOCYTES

(75) Inventor: Lawrence S. Lamb, Jr., Columbia, SC (US)

(73) Assignee: Palmetto Health Alliance, Columbia, SC (US)

( * ) Notice: Subject to any disclaimer, the term of this patent is extended or adjusted under 35 U.S.C. 154(b) by 483 days.

(21) Appl. No.: 09/879,398

(22) Filed: Jun. 12, 2001

(65) Prior Publication Data

US 2001/0051151 A1   Dec. 13, 2001

Related U.S. Application Data

(60) Division of application No. 09/616,865, filed on Jul. 14, 2000, now abandoned, which is a continuation of application No. PCT/US00/01867, filed on Jan. 27, 2000.

(60) Provisional application No. 60/117,718, filed on Jan. 28, 1999.

(51) Int. Cl.
  *A61K 35/14*   (2006.01)
  *G01N 33/49*   (2006.01)
  *G01N 33/574*  (2006.01)

(52) U.S. Cl. .................. 424/93.71; 424/534; 435/7.1; 435/7.24

(58) Field of Classification Search ............. 424/93.71, 424/534, 577; 435/325, 372.3, 373
See application file for complete search history.

(56) References Cited

U.S. PATENT DOCUMENTS 5,639,653 A   6/1997 Bloom et al.

FOREIGN PATENT DOCUMENTS

| EP | 0 786 664 A1 |   | 1/1996 |
|----|----|----|----|
| WO | WO 98/33891 | * | 8/1998 |
| WO | WO-98/33891 A |  | 8/1998 |
| WO | WO-99/46365 A |  | 9/1999 |

OTHER PUBLICATIONS

Coligan et al, Current Protocols in Immunology chapter 7.4, p. 7.4.1-7.4.6, 1995.*
Spitler et al, Cancer Biotherapy 10: 1-3, 1995.*
Bodey et al, Anticancer Research 20: 2665-2676, 2000.*
Esslin et al, J of National Cancer Institute 83: 1564-9, 1994.*
Sykes et al, Proc Nat. Acad. Sci 87: 5633-37, 1990.*
Falkenburg et al, J Immunotherapy 14(4): 305-9, Nov. 1993.*
O'Reilly RJ, Hansen JA, Kurtzberg J, Henslee-Downey PJ, Martelli M, Aversa F., Allogeneic marrow transplantation: approaches for the patient lacking a donor. In Schecter, G.P., and McArthur, J.R. (eds), Hematology 1996: Education Program for the American Society of Hematology, 132-46, discloses the use of T cell depletion to prevent graft-versus-host disease.
Henslee-Downey PJ, Abhyankar SH, Parrish RS, Pati AR, Godder KT, Neglia WJ, Goon-Johnson KS, Geier SS, Lee CG, Gee AP. Use of partially mismatched related donors extends access to allogeneic marrow transplant. Blood 89 (10):3864, 1997, discloses the increase in disease relapse upon the use of T cell depletion to prevent graft-versus-host disease.
Horowitz, M.M., Gale, R.P., Sondel, P.M., Goldman, J.M. et al. Graft versus leukemia reactions after bone marrow transplantation. Blood 75, 555, 1990, discloses that graft-versus-leukemia effectors are predominantly T cells that can either recognize allospecific molecules and cell surface molecules.
Sykes, M., Romick, M.L., Sachs, D.H. Interleukin 2 prevents graft-versus-host disease while preserving the graft-versus-leukemia effect of allogeneic T cells. Proc. Nat. Acad. Sci. 1990; 87: 5633, discloses evidence that graft-versus-host and graft-versus-leukemia effects can be separated to some degree.
Truitt, R.L., Atasoylu, A.A. Contribution of CD4+ and CD8+ T cells to graft-versus-host disease and the graft-versus-leukemia reactivity after transplantation of MHC compatible bone marrow Bone Marrow Transplantation 1991; 8: 51.
Viale M, Ferrini S, Bacigalupo A. TCR positive lymphocytes after allogeneic bone marrow transplantation. Bone Marrow Transplantation 10:249, 1992, discloses an increase in the ration of V 1:V 2 cells in patients with acute graft-versus-host disease.

(Continued)

*Primary Examiner*—Christina Chan
*Assistant Examiner*—Phuong N Huynh
(74) *Attorney, Agent, or Firm*—McNair Law Firm, P.A.

(57) ABSTRACT

Patients who develop increased numbers of γδ+ cytotoxic T lymphocytes 2–6 months after allogeneic bone marrow transplantation are less likely to relapse than those who do not. The γδ+ T cells isolated from blood of patients with increased γδ+ T cells are CD3+CD4−CD8−CD57+, cytolytic to K562 cells, and express the Vδ1 T cell receptor phenotype. Similar γδ+ T cells can be generated in vitro by culture of donor mononuclear cells which are enriched for γδ+ T cells by immunomagnetic depletion of depleted of CD4+ and CD8+ cells. This γδ-enriched cell preparation was cultured on a combination of immobilized pan-δ monoclonal antibody and irradiated recipient B cell leukemia. After four weeks, the cultures were almost exclusively Vδ1+CD3+ CD4−CD8− cells that co-expressed activation-associated antigens CD69, CD25, and HLA-DR. Furthermore, they were cytolytic against the primary leukemia obtained from the recipient and lymphoblastic leukemia cell lines, yet had minimal cytotoxicity against normal donor-derived mononuclear cells or myeloid leukemia cell lines. These observations suggest that donor-derived cytotoxic γδ+ T cells can be generated in vitro, and may provide therapeutic potential for prevention of disease relapse.

10 Claims, 9 Drawing Sheets

OTHER PUBLICATIONS

Yabe M, Yabe H, Hattori K, Hinorhars T, Morimoto T, Kato S, Kusonoki A. Transition of T-cell receptor gamma/delta expressing double negative (CD4/CD8) lymphocytes after allogeneic bone marrow transplantation. Bone Marrow Transplantation 14:741, 1994, discloses increases in the ration of CD4—CD8—gd+ T cells during post-bone marrow transplantation.

Tsuji S, Char D, Bucy RP, Simonsen M, Chen C, Cooper MD. +T-cells are secondary participants in acute graft-versus-host reactions initiated by CD4+ T-cells. European Journal of Immunology 26: 420, 1996, discloses gd+ T cells that are recruited into donor + lesions where they are activated and induced to proliferate.

Cela ME, Holliday MS, Rooney CM, Richardson S, Alexander B, Krance RA, Brenner MK, Heslop HE. + T-lymphocyte regeneration after T-lymphocyte-depleted bone marrow transplantation from mismatched family members or matched unrelated donors. Bone Marrow Transplantation 17:243, 1996, discloses the use of selective or targeted type of T cell delpletion combined with post-transplant immune suppression.

Esslin A, Formby B. Comparison of cytolytic and proliferative activities of human and T-cells from peripheral blood against various human tumor cell lines. Journal of the National Cancer Institute 83:1564, 1994, discloses that in vitro activated gd+ T cells can mediate broadly-based non-MHC restricted cytolytic activity to selected human tumor cell lines.

Orsini DL, VanGils M, Kooy YMC, Struyk L, Klein G, van den Elsen P, Koning F. Functional and molecular characterization of B-cell-responsive V 1+ T-cells. European Journal of Immunology 24:3199, 1994, discloses that gd+ T cells can recognize unprocessed peptides.

Hoffman, T., Theobald, M., Bunjes, D., Weiss, M., Heimpel, H., Heidt, W. Frequency of bone marrow T cells responding to HLA-identical non-leukemic and leukemic stimulator cells. Bone Marrow Transplantation 1993; 12: 1, discloses the generation of leukemia-reactive clones.

Fisch, P., Malkovska, M., Braakman, E., Sturm, E., Bolhuis, R.L., Prieve, A., Sosman, J.A., Lam, V.A., Sondel, P.M. Gamma/delta T cell clones and natural killer cell clones mediate distinct patterns of non-major histocompatibility-restricted cytolysis. J. Exp. Med. 1990; 171: 1567, discloses the identification of potential leukemia-associated antigens.

Kaur, I., Voss, S.D., Gupta, R.S., Schell, K., Fisch, P., Sondel, P.M. Human peripheral gamma/delta T cells recognize hsp60 molecules on Daudi Burkitt's lymphoma cells. J. Immunol. 1993; 150: 2046, discloses gd+ T cells response to heat shock proteins.

Potential antileukemic effect of gamma delta T cells in acute lymphoblastic leukemia. Leukemia 1995: 9: 863, discloses cytotoxic anti-leukemic activity in a patient by gd+ T cells expressing the V 1 form of the T cell receptor.

Lamb LS, Henslee-Downey PJ, Parrish RS, Godder KT, Thompson J, Lee C, Gee AP. Increased frequency of TCR-+ T-cells in disease-free survivors following T-cell depleted partially mismatched bone marrow transplantation for leukemia. Journal of Hematotherapy 5:503, 1996, discloses a higher percentage of survival among patients having an increased proportion of gd+ T cells as compared to patients have a normal number of gd+ T cells.

Lamb, L.S., Gee, A., Hazlett, L, Musk, P., Parrish, R.S., O'Hanlon, T.P., Geier, S., Folk, R.S., Harris, W.G., McPherson, K., Lee, C., Henslee-Downey, P.J. Influence of T cell depletion method on circulating gd+ T cell reconstitution and potential role in the graft-versus-leukemia effect Cytotherapy (in press), discloses that enrichment of a graft with gd+ T cells may contribute to later development of increased gd+ T cells.

Anasetti, C., Amos, D., Beatty, P.G., Appelbaum, F.R. et al. Effect of HLA compatibility on engraftment of bone marrow transplants in patients with leukemia or lymphoma. New Engl. J. Med. 1989; 320: 197, discloses that minor histocompatibility differences can initiate graft-versus-host disease.

Beatty, P.G., Clift, R.A., Mickelson, E.M., Nisperos, B.B. Flournoy, N., Martin, P.J., Sanders, J.E., Stewart, P., Buckner, C.D., Storb, R., Thomas, E.D., Hansen, J. Marrow transplantation from related donors other than HLA-identical siblings. New. Engl. J. Med. 1985; 313: 765, discloses that initial attempts to use non-manipulated marrow from mismatched unrelated donors and partially mismatched related donors have resulted in severe or fatal graft-versus-host disease.

Frame, J.N., Collins, N.H., Cartagena, T., Waldmann, H., O'Reilly, R., Dupont, B. & Kernan, N.A. T cell depletion of human bone marrow: comparison of Campath I plus complement, anti-T cell a-chain immunotoxin, and soybean agglutinin alone or in combination with sheep erythrocytes or immunomagnetic beads. Transplantation, 1989; 47: 984, discloses method for removing suspected mediators of the graft-versus-host disease from bone marrow ex vivo prior to infusion.

Kernan, N.A., Bordignon, C., Heller, G., Cunningham, I. et al. Graft failure after T cell depleted human leukocyte antigen identical marrow transplants for leukemia. Blood 1989; 74: 2227, discloses results from transplants in which patients received marrow that was highly depleted of T cells showing reduction in graft-versus-host disease and increase in graft failure.

Korngold, R. and Sprent, J. T cell subsets and graft-versus-host disease. Transpln Proc. 44, 335, 1987, discloses that both CD4 and CD8-positive cells are capable of mediating lethal graft-versus-host disease.

Ash, R.C., Horowitz, M.M., Gale, R.P., van Bekkum, J.T. et al. Bone marrow transplantation from related donors other than HLA-identical siblings: effect of T cell depletion. Bone Marrow Transplantation 7, 441, 1991 discloses that there was no overall improvement in leukemia-free survival from bone marrow transplantation using partially mismatched related donors.

Lee, C., Henslee-Downey, P.J., Brouilette, M., Pati, A.R., Godder, K., Abhyankar, S.H., Gee, A.P. Comparison of OKT-3 and T10B9 for ex vivo T cell depletion of partially mismatched related donor bone marrow transplantation. Blood 1996; 86: 625a, discloses the use of sequential immunomodulation of the patent and T cell depletion can result in stable engraftment in greater than 95% of recipients.

Goldman, J.M., Gale, R.P., Horowitz, M.M., Biggs, J.C., Champlin, R.E., Gluckman, E., Hoffman, R.G., Jacobsen, S.J., Marmot, A., M., McGlave, P.B., Messner, H.A., Rimm, A., A., Rozman, C., Speck, B., Tura, S., Weinger, R.S. & Bortin, M.M. Bone marrow transplantation for chronic myelogenous leukemia in chronic phase: Increased risk for relapse associated with T-cell depletion. Ann Int Med, 1988; 108; 806, discloses an increase in disease relapse when T cell depletion has been used in matched sibling transplantation.

Hesner, M.J., Endean, D., Caspter, J.T., Horowitz, M.M., Keever-Taylor, C.A., Roth, M., Flomenberg, N., Drobyski, W.R. Use of unrelated marrow grafts compensates for reduced graft-versus-leukemia reactivity after T cell depleted allogeneic marrow transplantation for chronic myelogenous leukemia Blood 1995; 86: 3987, discloses that the graft-versus-leukemia reaction is most effective in chronic myelogenous leukemia.

Slavin, S., Naparstek, E., Nagler, A., Ackerstein, A., Kapelushnik, J., Or, R. Allogeneic cell therapy for relapsed leukemia after bone marrow transplantation with donor peripheral blood lymphocytes. Exp. Hematol. 1995; 23: 1553, discloses graft-versus-leukemia reaction in acute leukemias.

Antin, J.H. Graft-versus-leukemia: no longer an epiphenomenon. Blood 1993; 82: 2273, discloses that T lymphocytes recognize and eliminate residual leukemia through both MHC restricted and non-restricted pathways.

Bigby, M., Markowitz, J.M., Bleicher, P.A., Grusby, M.J., Simha, S., Siebrecht, M., Wagner, M., Nagler-Anderson, C., Glimcher, L.H. most T cells develop normally in the absence of MHC class II antigens. J. Immunol. 1993; 151: 4465, discloses that gd+ T cells do not co-express CD4 and CD8, and may develop in the absence of MHC class II molecules.

Lanier, L. Unusual lymphocytes—T cells and NK cells. The Immunologist 1995; 3; 182, discloses that when gd+ T cell clones are obtained against peptide antigens, the peptide recognition is not restricted by classical MHC molecules.

Schild, H., Mavaddat, N., Litzenberger, C., Ehrlich, E.W., Davis, M.M., Bluestone, J.A., Matis, L., Draper, R.K. Chien, y. The nature of major histocompatibility complex recognition by + T cells. Cell 1994; 76: 29, discloses that gd+ T cells do not require presentation of antigens in the context of the MHC Class I or Class II molecules for activation.

Sperling, A.I., Linsley, P.S., Barrett, T.A., Bluestone, J.A. CD-28 mediated costimulation is necessary for the activation of T cell receptor- + T lymphocytes. J. Immunol. 1993; 151: 6043, discloses that gd+ T cells may require CD28-mediated co-stimulation for activation.

Wesselborg, S., Janssen, O., Pechhold, K., Kabelitz, D. Selective activation of / + T cells by single anti-CD2 antibodies. J. Exp. Med. 1991; 173: 297, discloses that gd+ T cells can be activated by anti-CD2 antibodies.

Avdalovic, M., Fong, D., Formby, B. Adhesion and costimulation of proliferative responses of human T cells by interaction of VLA-4 and VLA-5 with fibronectin. Immunol. Lett. 1993; 35: 101, discloses that gd+ T cells have been shown to adhere to fibronectin-coated plates via the VLA-4 receptor.

Lin, T., Matsuzaki, G., Umesue, M., Omoto, K., Yoshida, H., Harada, M., Singaram, C., Hiromatsu, K., Nomoto, K. Development of gd+ CD4 CD8+ but not TCR- CD4 CD8+ i-IEL is resistant to cyclosporin A. J. Immunol. 1995; 155: 4224, discloses that certain types of gd+ T cells may be resistant to cyclosporin A.

Ellison, C.A., MacDonald, G.C., Rector, E.S., Gartner, J.G. gd+ T cells in the pathobiology of murine acute graft-versus-host disease. J. Immunol. 1995; 155: 4189, discloses an increase in peripheral gd+ T cells of acute graft-versus-host disease following allogeneic non-T cell depletion bone marrow transplantation.

Blazar, B.R., Taylor, P.A. Bluestone, J.A., Vallera, D.A. Murine -expressing T cells affect alloengraftment via the reconognition of nonclassical major histocompatibility complex class Ib antigens. Blood 1996; 87: 4463, discloses that murine gd+ T cells can play a role in rejection, alloengraftment, and graft-versus-host disease through recognition of the certain MHC class Ib antigens.

Chouaib, F., Porto, P., Delorme, D., Hercend, T. Further evidence for a g/d T cell receptor-mediated TCT.1/CD48 recognition. J. Immunol. 147: 2864; 1991, discloses human alloreactive gd+ T cells recognizing antigens distributed on hematopoietic cells.

Hacker, G., Kromer, S., Falk, M., Heeg, K., Wagner, H., Pfeffer, K. V 1+ subset of human T cells responds to ligands expressed by EBV-infected Burkitt lymphoma cells and transformed B lymphocytes. J. Immunol. 149: 3984; 1992, discloses V 1 cell activation in EBV-transformed B cells and EBV-infected Burkitt lymphoma cells.

Marx. S., Wesch, D., Kabelitz, D. Activation of humn T cells by *Mycobacterium tuberculosis* and Daudi lymphoma cells. J. Immunol. 158: 2842; 1997, discloses V 1 cell activation in Daudi lymphoma cells.

"Studies in Patients with Chronic Myelogenous Leukemia," Leukemia Insights Newsletter, vol. 1, No. 2 Summer, 1995, original publication date unknown, at http://www3.mdanderson.org/leukemia/insight/letter12.html discloses investigational studies in late chronic phase chronic myelogenous leukemia.

* cited by examiner

FOLD EXPANSION MEASUREMENTS WERE TAKEN AFTER FOUR WEEKS OF CULTURE PRIOR TO HARVESTING WELLS FOR EXPERIMENTS AND CYROPRESERVATION

*EXPANSION OF γδ+T CELLS FROM DONOR #2 DID OCCUR, BUT WAS DELAYED. SUBSTANTIAL NUMBERS OF γδ+T CELLS WERE NOT SEEN UNTIL AFTER 4 WEEKS.

IN VITRO ACTIVATED γ δ LYMPHOCYTES

PRIORITY CLAIM

This application is a divisional of U.S. application Ser. No. 09/616,865, filed Jul. 14, 2000 now abandoned, which was a continuation of international application number PCT/US00/01867 filed Jan. 17, 2000 which claims priority to 60/117,718 filed Jan. 28, 1999.

BACKGROUND OF THE INVENTION

Allogeneic bone marrow transplantation (BMT) provides a potentially curative treatment for leukemias that are refractory to conventional therapy. In addition to providing hematopoietic rescue from myeloablative therapy, BMT offers an adoptive immunotherapy effect (graft-versus-leukemia-GvL) that can be beneficial in the elimination of residual leukemia. This was initially shown in cases where T cell depletion (TCD) has been used to prevent graft-versus-host disease (GvHD) but also experienced an increase in disease relapse (1). Indeed, relapse rates in high-risk patients (long-standing recurrent disease or relapse at the time of BMT) can be as high as 70% (2). Therefore, further improvement in disease-free survival is likely to depend on the antileukemic effectiveness of the transplant, i.e. maximizing the GvL effect.

Most experimental evidence suggests that GvL effectors are predominantly T cells that can either recognize allospecific molecules expressed on both normal and neoplastic hematopoietic cells or recognize cell surface molecules that are either unique to or preferentially expressed by the leukemia (3–7). Identification of specific cell populations that are important antileukemic effectors is an essential first step to successful GvL graft engineering and cellular immunotherapy.

Although several studies have suggested that γδ+ T cells may not be important primary effectors of GvHD (8–12), few have addressed the GvL potential of γδ+ T cells. Esslin (13) noted that in vitro activated γδ+ T cells can mediate broadly-based non-MHC restricted cytolytic activity to selected human tumor cell lines. Others have shown that γδ+ T cells can recognize unprocessed peptides, some of which are preferentially expressed on tumor cells (14–18). Finally, one report has shown cytotoxic anti-leukemic activity in a patient against B cell ALL by γδ+ T cells expressing the Vδ1 form of the T cell receptor (19). Taken together, these findings support a potential antileukemic role for γδ+ T cells.

Published data describing a series of 10 leukemia patients who developed an increased proportion of circulating CD3+CD4−CD8−Vδ1+γδ+ T cells between 60 and 270 days post-BMT from a partially mismatched related donor (PMRD) which continued for up to two years. Eight of these patients are surviving and remain free of disease, as compared to a DFS probability of 31% at 2.5 years among 100-day survivors with a normal number of γδ+ T cells (20). In addition, it has been recently shown that enrichment of the graft with γδ+ T cells may have contributed to the later development of increased γδ+ T cells (21). Regardless of the TCD protocol used, however, patients who developed increased γδ+ T cells showed the same cell phenotype and cytolytic function as well as a decreased incidence of relapse.

Allogeneic Bone Marrow Transplantation and Graft-Host Interactions: High-dose chemo/radiotherapy followed by bone marrow rescue provides a potentially curative treatment for a variety of leukemias and solid tumors that are refractory to conventional therapy. An alloreactive response, mediated by donor immunocompetent cells in the graft and directed against normal cells and tissues in the recipient can result in the development of graft-versus-host disease (GvHD). GvHD can occur in up to 50% of patients receiving unmodified, HLA-identical marrow, indicating that minor histocompatibility differences, not detected by conventional HLA matching techniques, can initiate this reaction (22, 23). For the majority of patients (approximately 70%) who do not have matched sibling donor (MSD) alternative donors may be used but the risk of acute GvHD is increased due to differences in major as will minor histocompatibility antigens (1). The same alloreactive response, however, can be beneficial in the elimination of residual leukemia through an adoptive immunotherapy mechanism known as the graftversus-leukemia (GvL effect).

Allogeneic BMT and the use of Alternative Donors: In most instances, the ideal bone marrow donor is the HLA-identical sibling. Alternative donors include the HLA-phenotypically matched unrelated donor (MUD), a partially mismatched related donor (PMRD) or a cord blood donor (CBD), who can be a phenotypically matched or mismatched related or unrelated donor (1).

Graft engineering, T cell depletion, and graft-host interactions: Initial attempts to use non-manipulated marrow from MUDs and PMRDs have resulted in severe or fatal GvHD (24, 25). This stimulated the development of methods to remove the suspected mediators of GvHD (T lymphocytes) from the marrow ex vivo prior to infusion (26). Results from transplants in which patients received marrow that was highly depleted of T cells (pan-T cell depletion) were initially promising, in that GvHD was significantly reduced; however, this was accompanied by an increase in graft failure (27, 28), suggesting that donor T cells may eliminate the ability of residual recipient T cells to reject the graft.

Animal studies of PMRD transplants have indicated that both CD4 and CD8-positive cells are capable of mediating lethal GvHD (29). Initial human studies have therefore used ex vivo pan-T cell depletion to engineer these grafts. This has either been achieved by agglutination with soybean lectin and rosetting the residual T cells with sheep red blood cells, or by use of T cell-directed MAbs, e.g. anti-CD2, CD3, CD5, in combination with panning or complement to eliminate antibody-sensitized cells (26). In a study comparing 470 PMRD reduced the risk of acute GvHD, but increased the risk of graft failure, and there was no overall improvement in leukemia-free survival (30). Therefore, aggressive ex vivo pan-TCD was felt not to be optimal in facilitating PMRD BMT, and subsequent studies have explored the use of a modified pan-T cell depletion that leaves more T cells in the graft. Another option is the use of a more selective or targeted type of TCD often combined with post-transplant immune suppression (11–13).

When T cell depletion (TCD) has been used in matched sibling transplantation, a further concern has been an increase in disease relapse seen particularly in patients with CML (33). This apparent disruption in the graft-versus-leukemia (GvL) effect has discouraged investigators from using TCD other than when MHC-nonidentical grafts are used. We have, however, shown that the use of sequential immunomodulation of the patient and T cell depletion of up to 3 Ag PMRD grafts can result in stable and sustained engraftment in >95% of recipients with a low incidence of acute and chronic GvHD (32). Relapse rates in high-risk patients (long-standing recurrent disease or relapse at the time of BMT) can be as high as 70% (2). This indicates that even though it is possible to cross major histocompatibility barriers with successful engraftment and a low incidence of GvHD, further improvement in disease-free survival will depend on the antileukemic effectiveness of the transplant. While this might be accomplished by performing the transplant earlier in the disease course, many patients will not be referred for allogenic BMT until they have demonstrated resistance to conventional-dose therap. Thus, enhancement of the GvL effect may be an essential component of the curative potential of allogeneic BMT.

Biology of the GvL Effect: The GvL reaction is thought to be most effective in chronic phase CML (34, 35), although there is also evidence for a GvL effect in the acute leukemias (36). It is generally thought that T lymphocytes recognize and eliminate residual leukemia through both MHC restricted and non-MHC restricted pathways (37). Targets for GvL include minor and/or major mismatched histocompatibility antigens and/or leukemia specific antigens. (38, 39). Every allogenic BMT patient potentially could benefit from the alloreactive response, although the extent of this benefit varies depending on whether the leukemia expresses allogenic antigens to a degree that triggers recognition and killing.

T cell recognition of leukemia-associated antigens is also thought to be a potentially important means by which immunocompetent cells may recognize and eliminate residual leukemia. It is known that leukemia-reactive clones can be generated (15). Specific targets for leukemia-reactive clones remain the topic of intense investigation, and some potential leukemia-associated antigens have been identified (3, 16–19) and are discussed below. The ability to identify and stimulate a GvL effect via either or both of these mechanisms may be of therapeutic importance in reducing the risk of relapse in patients who have received TCD grafts.

γδ+ T lymphocytes: Five to ten percent of T cells in normal peripheral blood bear the γδ receptor (42), although this number may be slightly higher in Asians and Blacks. Recent observations suggest that γδ+ T cells play a substantially different role in the immune system than that of αβ+ T cells. One of the most obvious differences is that most γδ+ T cells usually do not co-express CD4 or CD8, and therefore may develop normally in the absence of MHC class II molecules (43) since positive selection may not be required. Similarly, it is difficult to elicit a response of γδ+ T cells against allogeneic MHC class I or II antigens, and when it has been possible to obtain γδ+ T cell clones against peptide antigens, recognition of these peptides is usually not restricted by classical MHC molecules (44). In addition, γδ+ T cells tend to recognize intact rather than processed polypeptide (44).

While the requirements for activation of human γδ+ T cells are still poorly understood, it is clear that they are different from those of αβ+ T cells. γδ T cells do not require presentation of antigens in the context of the MHC Class I or Class II molecules for activation (45), however, they probably require CD28-mediated co-stimulation, and, following activation, show autocrine IL-2 production (46). They can also be activated by anti-CD2 antibodies (47). γδ+ T cells which express CD25 have also been shown to adhere to fibronectin-coated plates via the VLA-4 receptor with subsequent expansion, and cross linking of VLA-4 and VLA-5 receptors result in co-stimulated expansion induced by an anti pan-δ monoclonal antibody (48). Recent evidence has also suggested that certain subtypes of γδ+ T cells, predominantly the γδ+CD8αα+ homodimer population, may be resistant to Cyclosporin A (49).

Potential role of TCR-γδ+ T lymphocytes in allogenic BMT: While activation mechanisms for γδ+ T cells are just being elucidated, even less is known about the role of these cells in graft-host interactions. Ellison (50) reported an increase in peripheral γδ+ T cells in murine studies of acute GvHD following allogeneic non-TCD BMT (50). In that study, depletion of γδ+ T cells resulted in a significant decrease in GvHD-related mortality. Blazar (51) also has shown that murine γδ+ T cells can play a role in rejection, alloengraftment, and GvHD through recognition of the "nonclassical" MHC class Ib antigens.

Studies in humans have to this point been in conflict with murine studies. Norton (8) did not find γδ+ T cells to be effectors of epidermal damage in cutaneous GvHD. Viale (9) did note an increase in the ratio of Vδ1:Vδ2 cells in patients with acute GvHD but the significance of this finding remained undetermined. Tsuji (11) showed that although γδ+ T cells cannot produce GvHD on their own, host γδ+ T cells were recruited into donor αβ+ lesions where they were activated and induced to proliferate. Transitory increases in the ratio of CD4⁻CD8⁻γδ+ T cells have been reported during the first four weeks post-BMT in patients treated by GM-CSF, but the cells return to normal levels within eight weeks post-BMT (10). In addition, increased γδ+ T cells have been found in one (study to be associated with viral and fungal infections during the first year following TCD BMT in patients receiving either PMRD or MUD grafts (12). In the same study, increases in γδ+ T cells were not found to be associated with GvHD.

The potential for a possible anti-tumor role for γδ+ T cells was established by Esslin (13), who noted that in vitro activated peripheral blood γδ+ T cells posses cytolytic activity to selected human tumor cell lines when compared to similarly activated αβ+ T cells. This reactivity was not MHC restricted, but was dependent on interaction with LFA-1b/ICAM1 rather than the γδ receptor. These cells predominantly expressed the Vγ9/Vδ2 form of the T cell receptor. Proliferate responses of both αβ+ and γδ+ T cells, however, were inhibited by MAbs to anti-HLA-A, -B, and -C. These findings suggest that γδ+ T cells activated through the TCR have an advantage in non-MHC restricted cytolysis which may correlate with a GvL response. It is known that γδ+ T cells respond to heat shock proteins (16–18), some of which may be expressed by lymphomas. Human alloreactive γδ+ T cells have also been generated which recognize TCT.1 (Blast-1/CD48), an antigen broadly distributed on hematopoietic cells (52). These γδ+ T cells preferentially expressed the Vγ3/Vδ1 form of the T cell receptor. Vδ1+ cell activation has also been reported in response to EBV-transformed B cells (14, 53), EBV-infected Burkitt lymphoma cells (53), and Daudi lymphoma cells (54). In addition, one recent report has shown cytotoxic anti-leukemic activity in a patient against B cell ALL by γδ+ T cells expressing the Vδ1 form of the T cell receptor (19).

We have been able to expand in vitro donor-derived γδ T cells which have a striking resemblance to those seen in the patients described above. Donor mononuclear cells were depleted of CD4+/CD8+ T cells, and expanded on a combination of immobilized pan-δ monoclonal antibody and irradiated recipient B cell leukemia. After initial culture and re-stimulation, the cultures expanded rapidly and contained almost exclusively Vδ1+γδ+ T cells which expressed CD3, CD25, and CD69, but were CD4– and CD8– which are cytolytic to recipient leukemia and K562 cells but are minimally cytolytic to self MNC and third party leukemia. These observations suggest that donor-derived γδ+ T cells can be generated in vitro, thus providing a potential mechanism for cellular immunotherapy of leukemia.

DESCRIPTION OF THE PREFERRED EMBODIMENTS

Experimental Protocols

Donor/recipient pairs: Three patients who presented for BMT with relapsed acute lymphoblastic leukemia or induction failure and their HLA-partially mismatched related donors were enrolled in this study.

Cell preparation: For recipients, sufficient blood was drawn to obtain a minimum of $2.5 \times 10^7$ leukemic cells, but less than 50 ml, prior to the start of pre-BMT conditioning therapy. Leukemic cells from the recipient were separated from normal mononuclear cells (MNC) using density gradient centrifugation on Percoll using 30–40% gradient. If necessary, further purification was accomplished by immunomagnetic depletion of normal T and NK cells. Purity of normal and blast monolayers were evaluated by flow cytometry using MAbs previously found to be diagnostic for the patient's leukemia. The cells were then cryopreserved at a concentration of $20 \times 10^6$/ml in AIM-5 medium (Gibco) with 15% fetal bovine serum (Gibco) and 10% DMSO and stored in liquid nitrogen until donor selection was complete. Up to 50 ml of peripheral blood was then obtained from the corresponding partially mismatched related donor. These donor-derived γδ+ T cells were purified in the MNC layer by negative selection using CD4+ and CD8+ immunomagnetic microspheres (Dynal) at a ratio of 5 microspheres:cell. Removal of CD4+ and CD8+ cells from peripheral blood effectively depleted >95% of αβ+ T cells. The number of γδ+ T cells in the preparation and the effectiveness of the αβ+ T cell depletion was monitored by flow cytometry as described below using fluorochrome-conjugated antibodies to TCR-αβ, TCR-γδ, CD4, CD8, and CD3 (Becton-Dickinson Immunocytometry Systems-BDIS; San Jose, Calif.).

Culture and activation of γδ+ T cells: Cytotoxic γδ+ T cells were generated from donor-recipient pairs as follows: Tissue culture-treated 24 well plates were coated with 10 μg TCR-δ1 pan-δ monoclonal antibody (Endogen; Woburn, Mass.) in 300 μg PBS for 24 h at 4° C. to facilitate initial activation and expansion of γδ+ T cells as described by Esslin (13). Irradiated (50 Gy) primary leukemic blasts that were obtained and cryopreserved prior to BMT were thawed, washed ×3, and re-suspended in AIM-5 Media with 15% FBS and 25 IU of IL-2 at a concentration of $1.0 \times 10^6$ cells/ml. Aliquots of 1 ml of this suspension were plated on the coated wells. Following immunomagnetic depletion of CD4+ and CD8+ cells as described above, remaining donor-derived MNC were adjusted to a concentration of $1.0 \times 10^6$ cells/ml, and aliquots of 1 ml were added to the previously plated recipient blasts. Control wells consisted of CD4+ CD8+ depleted MNC plated on TCR-δ1 monoclonal antibody in the absence of blasts or blasts in the absence of monoclonal antibody. The cultures were examined daily for characteristic morphology of proliferating clusters. Media was refreshed twice weekly or as necessary dependent on the robustness of proliferation as determined by microscopic examination and the phenol red pH indicator in the media. After two weeks in culture, cells were photographed, and subcultured 1:2 or 1:4 as necessary onto a freshly coated plate. The γδ+ T cell + blast wells were restimulated with freshly thawed blasts at the same concentration used previously and assayed at this time and weekly thereafter for phenotype, Vδ subtype, and absolute cell number. At week four, fold expansion was calculated and harvesting was begun for phenotypic, molecular, and functional assays described below and for cryopreservation and storage as described above for future study. These assays were performed at 4–6 weeks of culture. The concentration of γδ+ T cells measured on a biweekly basis determined the degree of γδ+ T cell stimulation for each culture condition. When necessary, proliferating cells were transferred onto pan-δ MAb-coated tissue cultured flasks (Becton Dickinson) and cultures were maintained for up to twelve weeks, at which time no further proliferation was observed.

Flow cytometry: Expanded/activated γδ+ T cells were analyzed by four color flow cytometry for expression of CD45, CD3, CD4, CD8, CD19, CD56, CD25, HLA-DR, CD69 (Becton Dickinson Immunocytometry Systems; San Jose, CA-BDIS), and Vδ1 (Endogen, Woburn, Mass.), TCR-γδ, CD57, CD94, and Vδ1-Vδ3 (Coulter Immunotech; Miami, Fla.) using monoclonal antibodies conjugated with fluorescein isothiocyanate (FITC), phycoerythrin (PE), peridinin chlorophyll protein (PerCP), or allophycocyanan (APC). Recipient primary B cell leukemias were analyzed for expression of CD19, CD10, CD45, CD7, CD20, CD23, sIgGκ, sIgGλ, HLA-ABC, and HLA-DR (all from BDIS). At least 50,000 ungated events were collected in a list mode file and cell subpopulations in the lymphocyte CD45/side scatter gate and CD3/side scatter gate are quantitated and expressed as a percentage of the total lymphocyte population. Analysis was performed on a FACS Calibur flow cytometer using CellQuest software (BDIS).

Flow cytometric binding assays. Binding of donor γδ+ T cells to specific targets was examined by flow cytometry. Donor γδ+ T cells were incubated in AIM-5 Media with 15% FBS for 30 minutes at 37° C., centrifuged, and resuspended in phosphate-buffered saline. The cell suspension was labeled with one MAb specific for the leukemia but not expressed on γδ+ T cells (CD19) and anti-TCR γδ, which is not expressed on the leukemia. The cell preparation was incubated at 4° C. for 30 min, washed ×3, and analyzed by flow cytometry as detailed above. Clusters which were positive for both CD19 and γδ were then examined for forward (FSC) and side scatter (SSC) to determine if the represented multi-cell clusters. Dual-positive cells with increased FSC and SSC were scored as bound blast/γδ+ T cell clusters. Controls consisted of cultures of resting and activated donor γδ+ T cells co-cultured K562 cells. K562 cells are autofluorescent, so labeling with a flurochrome was unnecessary. Resting γδ+ T cells do not bind K562 while activated γδ+ T cells do.

Cytotoxicity assays: Third-party mononuclear cells, K562 erythroleukemia cells, and recipient primary leukemia were used as targets. Aliquots of target cells were labeled overnight with 3,3'-dioctadecyloxacarbocyanine (DiOC$_{18}$) (Molecular Probes, Eugene, Oreg.). The cells were then washed in phosphate buffered saline (PBS) and resuspended in RPMI-1640 with 10% fetal bovine serum (FBS) at a concentration of $2 \times 10^4$ cells/mi. Control MNC and expanded γδ+ T cells were suspended in RPMI-1640 and diluted to yield E:T ratios of 40:1–2.5:1 and added to the target cells. Aliquots of 130 μl counterstaining solution consisting of propidium iodine (PI) and PBS (Molecular Probes) were then added to the cell mixtures. The tubes were pelleted by centrifugation at 1000×g for 30 sec and then incubated for 4 hours. Following incubation, the tubes were acquired in a FACS Calibur flow cytometer (BDIS) and analyzed for green fluorescence (DiOC$_{18}$-560 nm) and red fluorescence (PI-630 nm). Analysis on a two parameter histogram allows separation of live target cells (DiOC$_{18}$+PI−) and membrane-compromised targets are (DiOC$_{18}$+PI+) from which % cytotoxicity was calculated.

γδ T cell Receptor Characterization: The clonal heterogeneity of γδ+ T cells determined by flow cytometry was further evaluated using molecular approaches to assess γδ TCR variable gene expression using peripheral blood mononuclear cells (PBMC) collected from the BMT donors and the expanded γδ+ T cells from derived from culture on the pan-δ MAb and co-culture with the recipient ALL. Total RNA was extracted from MNC or cultured cells by the acid-phenol guanidinium thiocyanate method (55) and reverse transcribed according to the GeneAmp RNA PCR protocol (Perkin-Elmer Cetus, Norwalk, Conn.). The cDNA product served as template for PCR amplifications utilizing γδ TCR gene family-specific primers according to established methods (56). PCR amplification products were analyzed by agarose gel electrophoresis in order to determine the number and identity of γδ TCR V gene families expressed in each sample. This analysis was facilitated by DNA blot hybridization with corresponding TCR Cγ- or Cδ-horseradish peroxidase (HRP) conjugated oligonucleotide probes followed by chemiluminescent detection (23). Amplified products were resolved on 4% sequencing gels and detected, due to the incorporation of fluorescent primers during amplification, using the Hitachi FMBIO-100 Fluorescent Imager or the ABI 377 (Perkin-Elmer) automated sequencer using Genescan™ software. This method (known as TCR spectratyping) provides a more refined assessment of γδ TCR clonal diversity in the specimens.

Results

Figure 1:
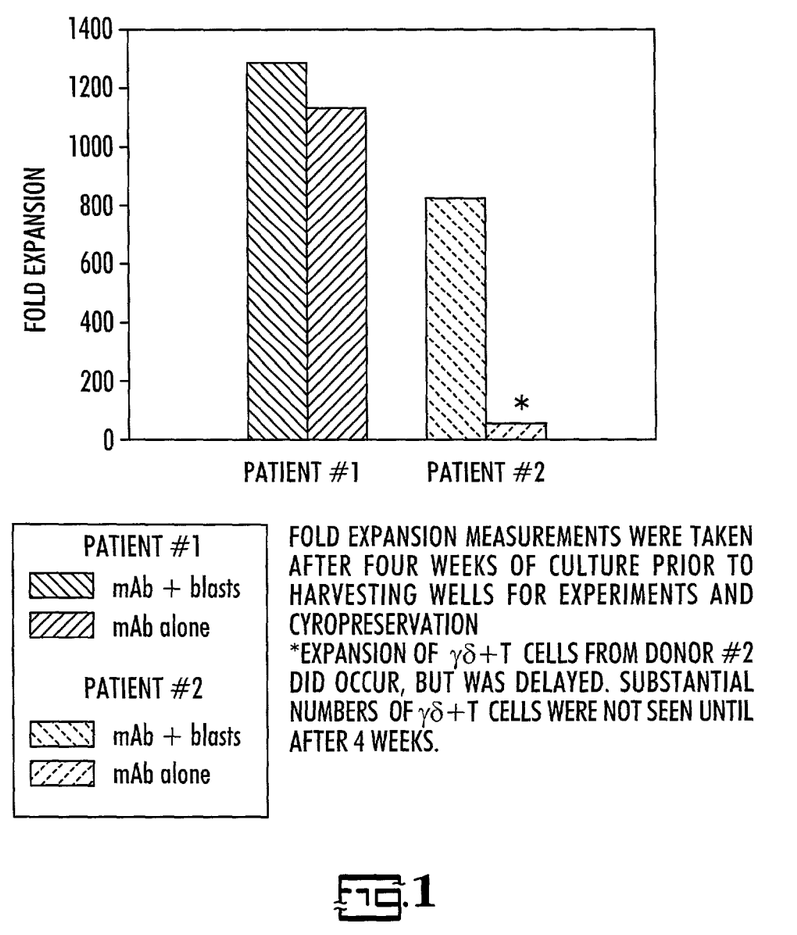
FIG. 1 shows the expansion of donor γδ+ T cells in culture.
Figure 2:
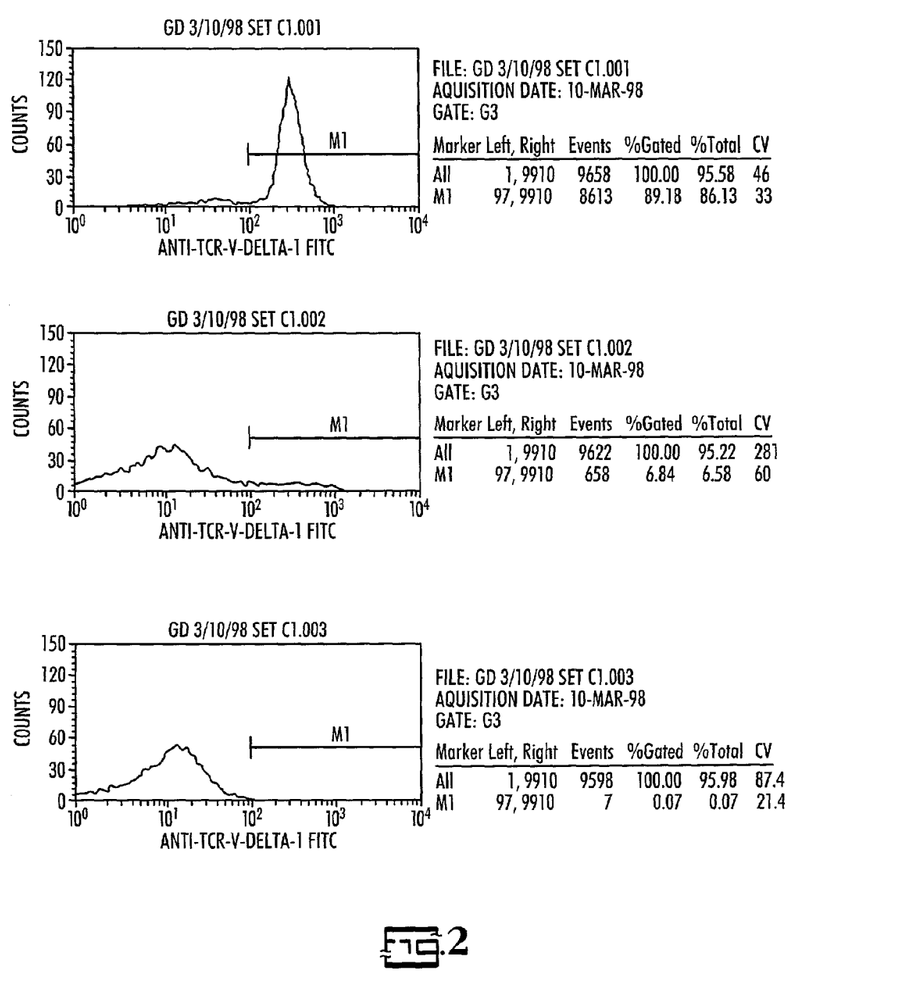
FIG. 2 shows the phenotypic analysis of proliferating γδ+ T cells from cultures on pan-δ MAb with blasts.
Figure 3:
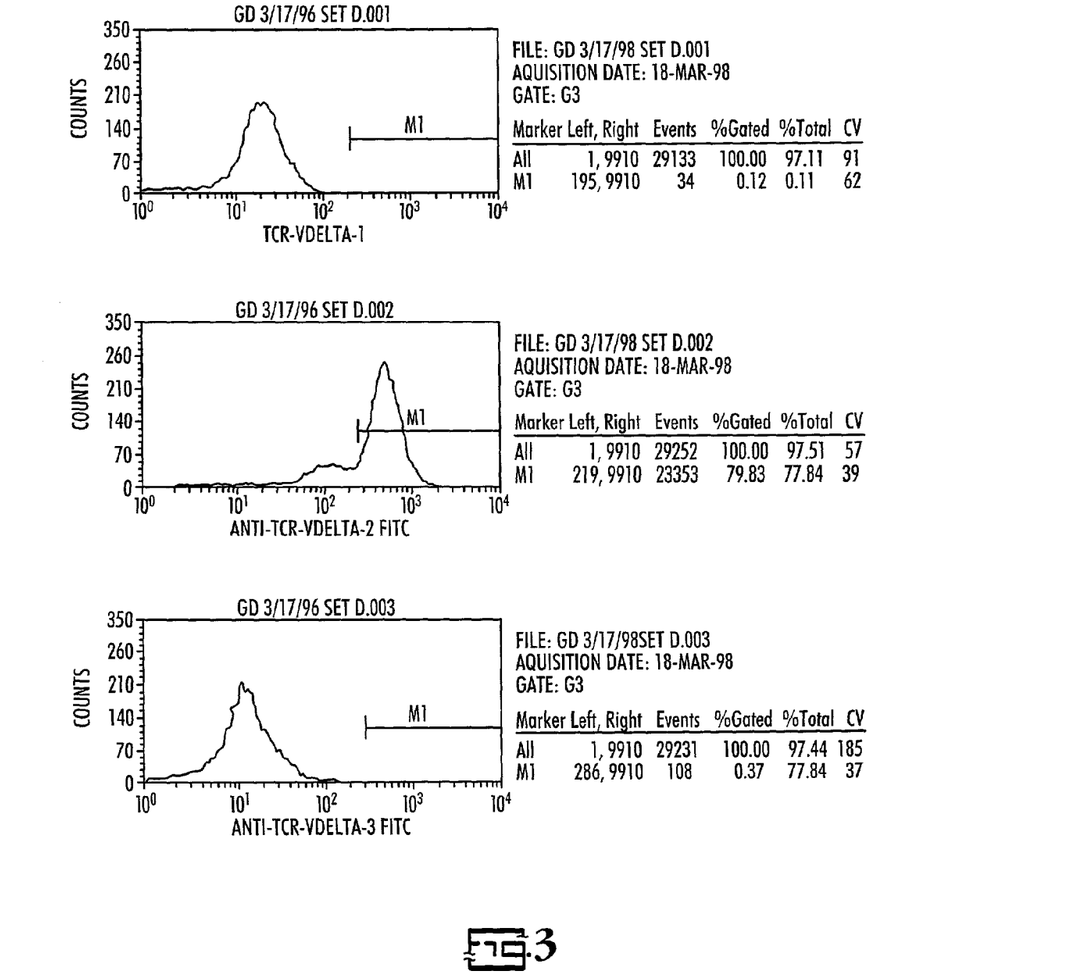
FIG. 3 shows the phenotypic analysis of proliferating γδ+ T cells from cultures on pan-δ MAb without blasts.
Figure 4:
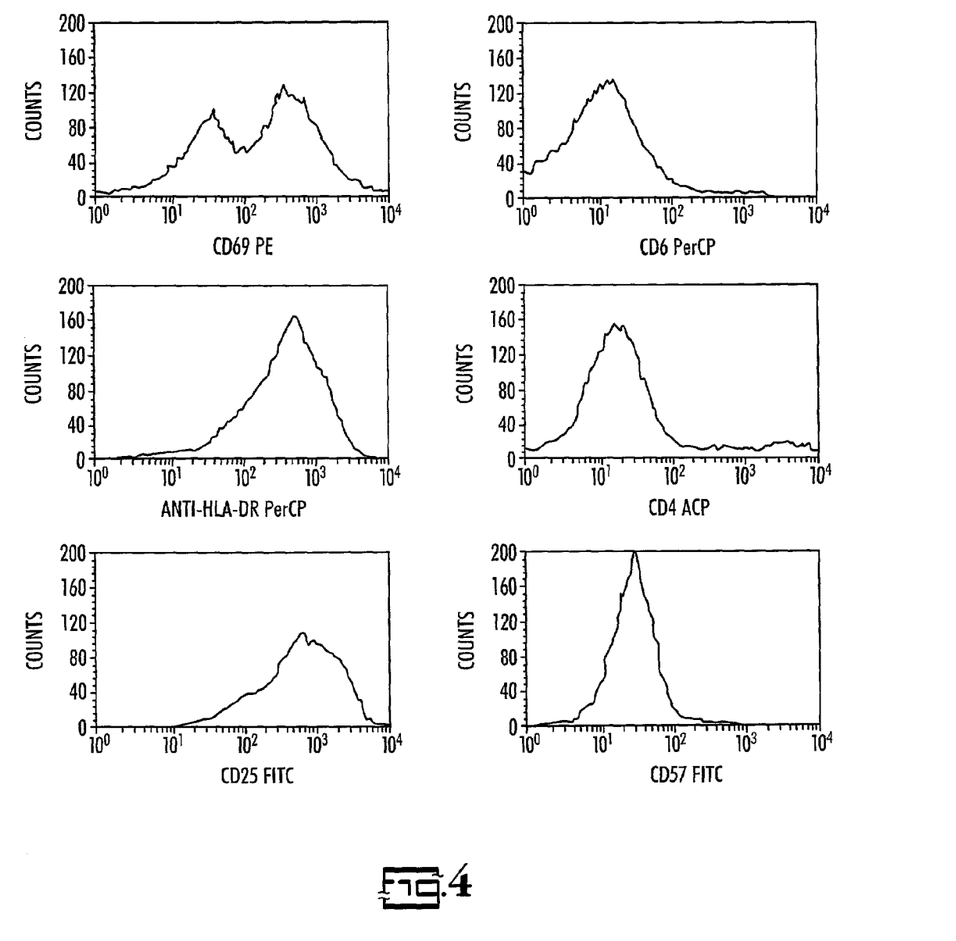
FIG. 4 shows the phenotype of γδ+ T cells from Patient #1.
Figure 5:
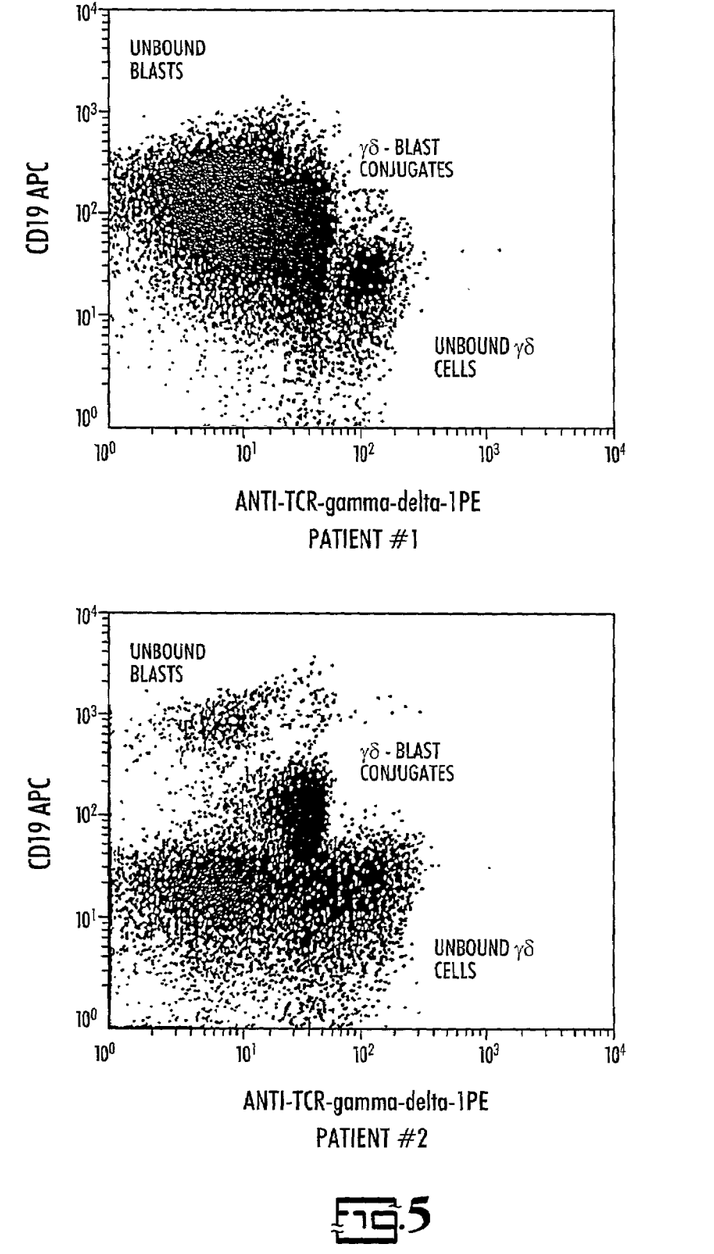
FIG. 5 shows the flow cytometric binding assay depicting the binding of activated donor γδ+ T cells to recipient leukemic CD19+ blasts.
Figure 6:
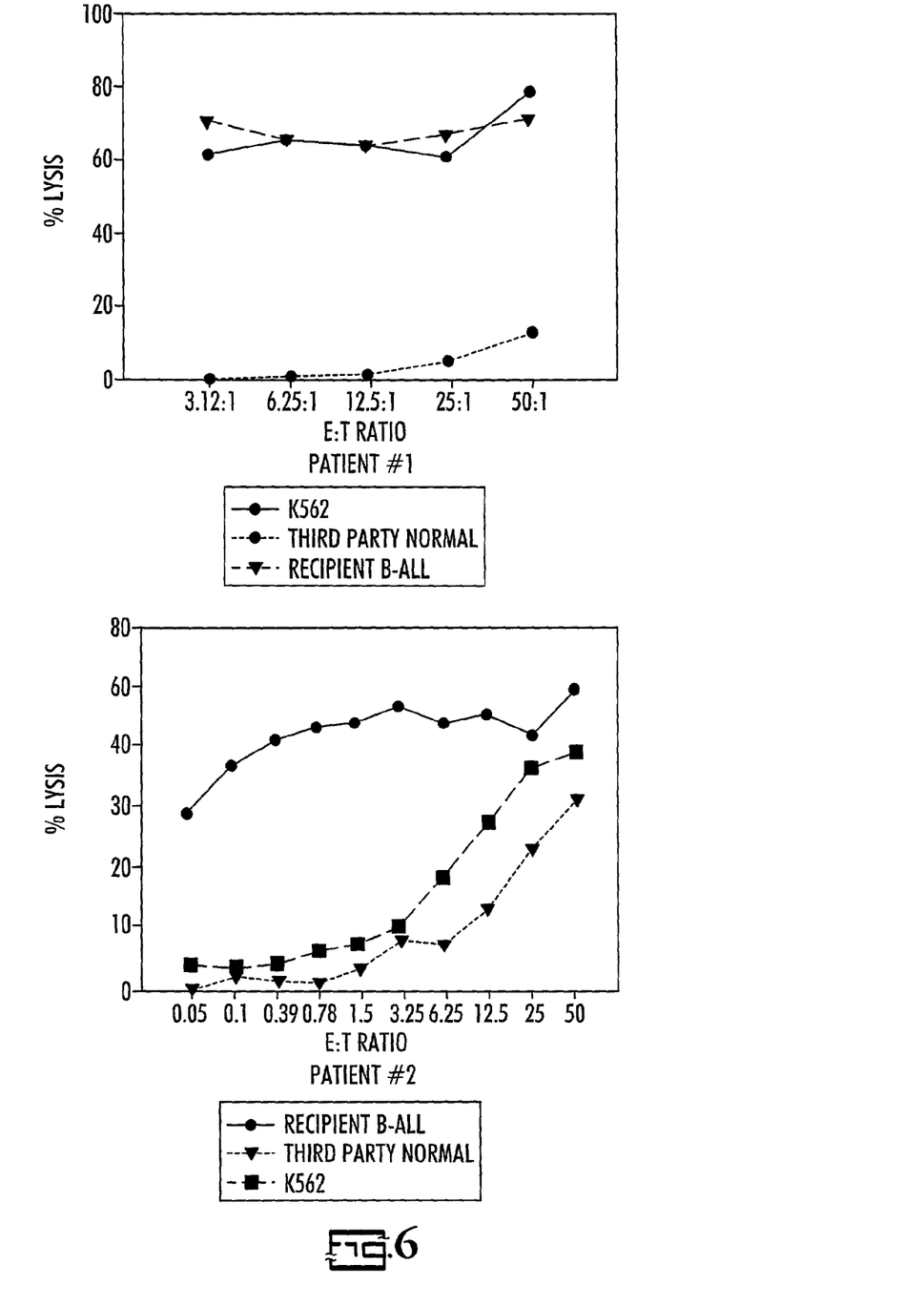
FIG. 6 shows the cytotoxicity of donor γδ+ T cells.
Figure 7:
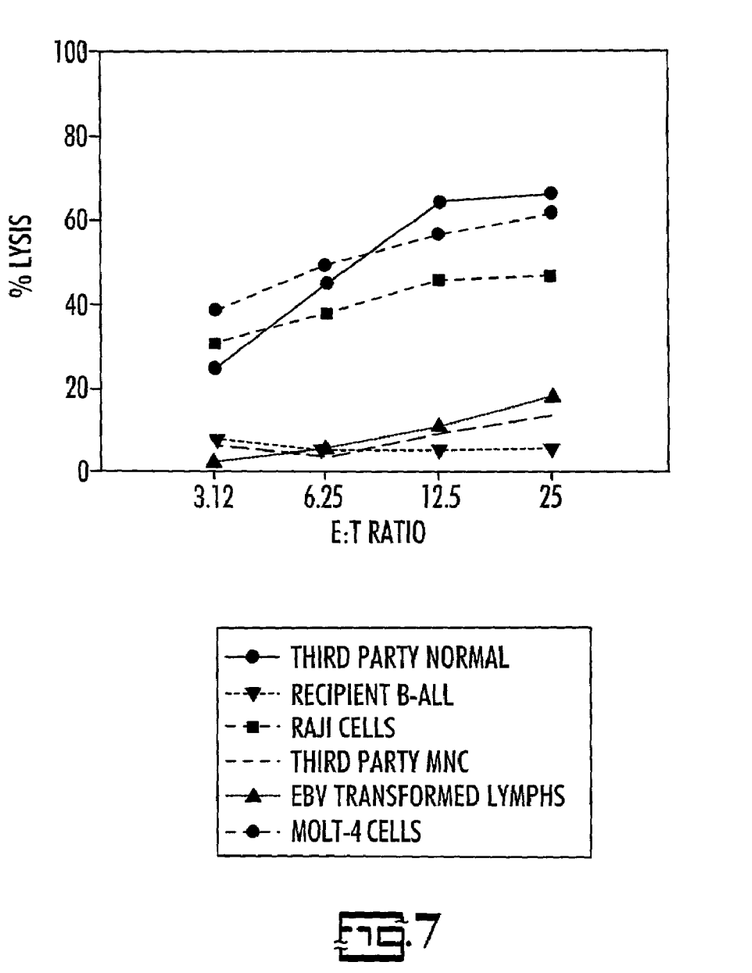
FIG. 7 shows the cytotoxicity of expanded γδ+ T cells against various cell lines.
Figure 8:
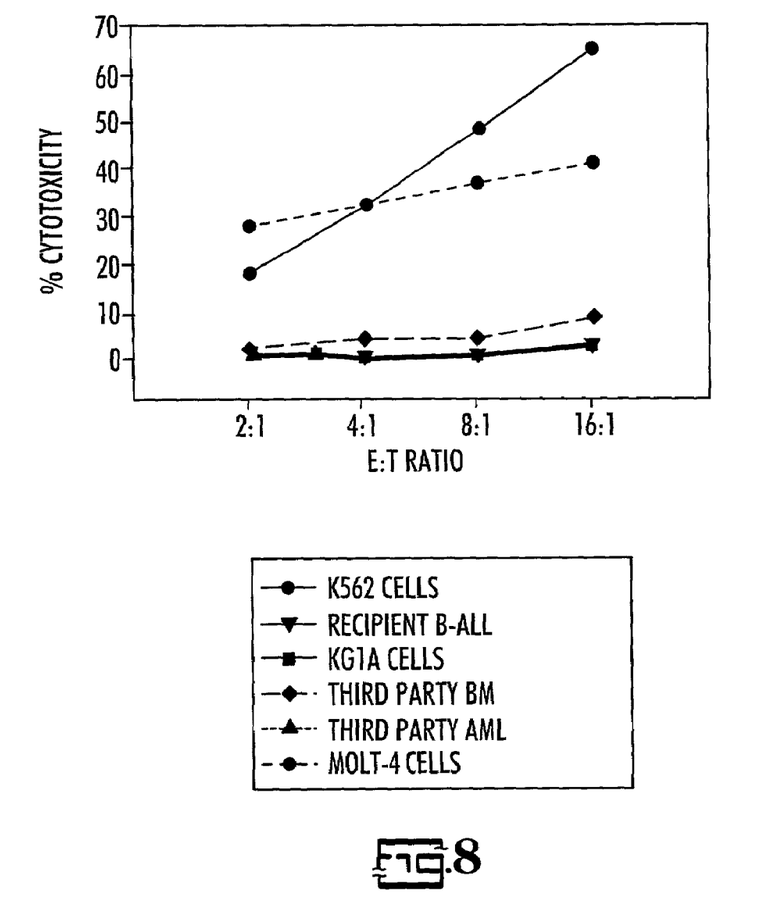
FIG. 8 shows the cytotoxic effects of expanded γδ+ T cells against other cell lines.
Figure 9:
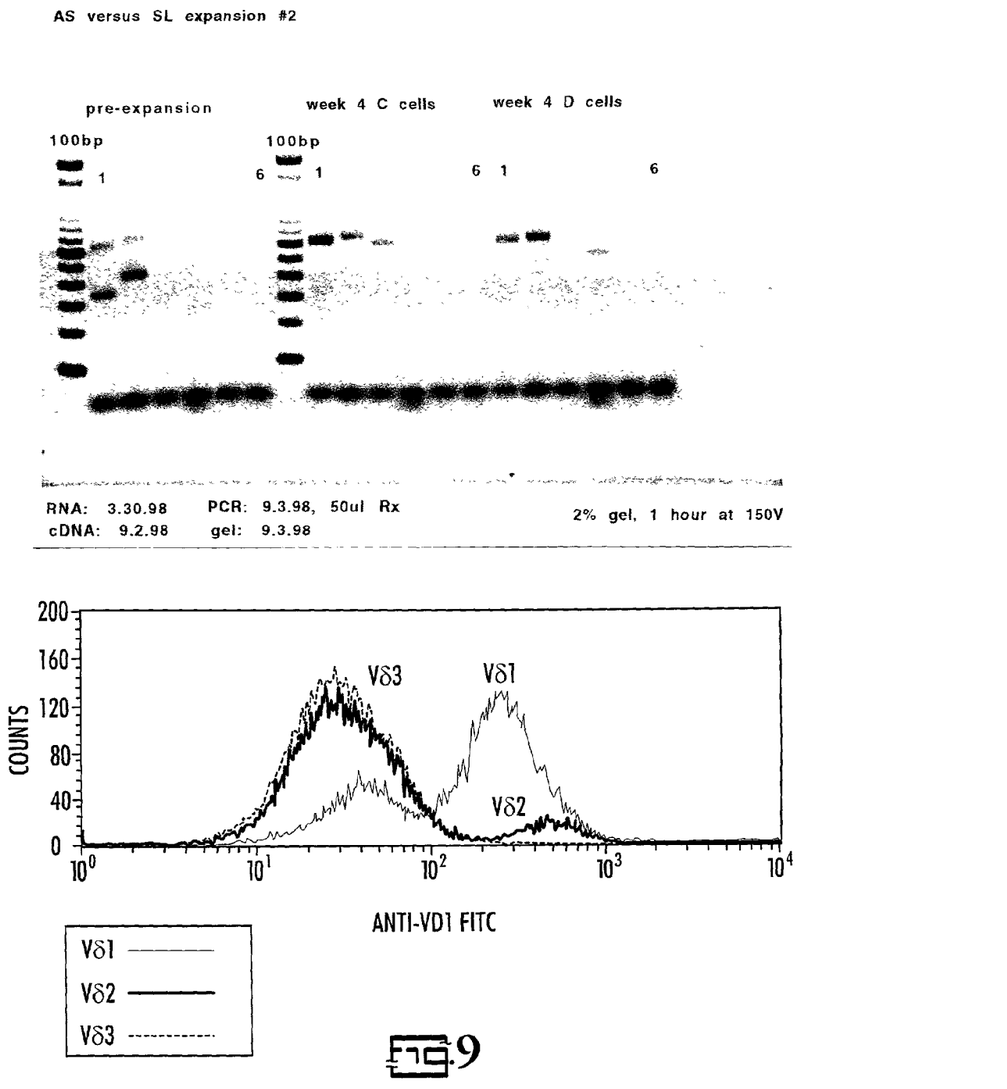
FIG. 9 shows the mRNA and surface expression of Vδ subtypes.

Immobilized pan-δ MAb alone and with and leukemic blasts stimulate γδ+ T cells. As shown in FIG. 1, γδ+ T cells strongly proliferated in response to immobilized pan-δ MAb alone and a combination of immobilized pan-δ MAb and blasts. Leukemic blasts alone did not support sustained proliferation of γδ+ T cells. It should be noted, however, that in one experiment γδ+ T cell proliferation occurred later in the culture than in the other two experiments. Immunophenotypic analysis of proliferating γδ+ T cell cultures. Phenotypic analysis revealed that proliferating γδ+ T cells from cultures on pan-δ MAb with blasts preferentially expressed Vδ1 (FIG. 2) while γδ+ T cells proliferating on pan-δ MAb without blasts preferentially expressed Vδ2 (FIG. 3). The γδ+ T cell cultures were predominantly CD3+CD4−CD8− and expressed activation-associated antigens CD69, CD25, and HLA-DR regardless of culture conditions (FIG. 4). Functional analysis of γδ+ T cell cultures. Cultured donor-derived γδ+ T cells from both culture methods were tested for their ability to bind and to lyse primary leukemia from the corresponding BMT recipient. FIG. 5 shows that indeed donor γδ+ T cells will bind recipient leukemia. Donor γδ+ T cells were highly cytotoxic to recipient leukemia as well as the NK sensitive target cell line K562 (FIG. 6). In one experiment, mild nonspecific cytotoxicity was seen against third party MNC. Different lytic profiles were seen which correlated with culture method and predominant Vδ gene usage (FIGS. 7 & 8). Vδ1+ cells cultured on immobilized pan-δ MAb and recipient blasts lysed primary ALL from the recipient and K562 cells as well as lymphoid cell lines, but had essentially no activity against myeloid cell lines. In contrast, Vδ2 clones from cultures expanded on pan-δ MAb alone showed cytotoxic activity against all targets. TCR repertoire analysis of γδ+ T cells. Polyclonal γδ+ T cells from the healthy BMT donors expressed mRNA predominantly for Vδ2 followed by Vδ1 and the Vδ3 (FIG. 9). Occasionally mRNA for Vδ4 and Vδ5 was seen. Examination of the Vδ repertoire of γδ cells cultured on pan-δ MAb alone was essentially unchanged from the peripheral blood Vδ repertoire. In contrast, γδ+ T cells cultured on pan-δ MAb and blasts showed preferential expression of Vδ1, followed by Vδ2 and Vδ3. High resolution analysis of these PCR products revealed.

It will be apparent to those of ordinary skill in the art that many modifications and substitutions can be made without departing from the spirit and the scope of the present invention.

REFERENCES

1. O'Reilly R J, Hansen J A, Kurtzberg J, Henslee-Downey P J, Martelli M, Aversa F., Allogeneic marrow transplantation: approaches for the patient lacking a donor. In Schecter, G. P., and McArthur, J. R. (eds), *Hematology 1996: Education Program for the American Society of Hematology*, 132–46.

2. Henslee-Downey P J, Abhyankar S H, Parrish R S, Pati A R, Godder K T, Neglia W J, Goon-Johnson K S, Geier S S, Lee C G, Gee A P. Use of partially mismatched related donors extends access to allogeneic marrow transplant. *Blood* 89 (10):3864, 1997.

3. Horowitz, M. M., Gale, R. P., Sondel, P. M., Goldman, J. M. et al. Graft versus leukemia reactions after bone marrow transplantation. Blood 75, 555, 1990.

4. Henslee, P. J., Thompson, J. S., Romond, E. H., Doukas, M. A. et al. T cell depletion of HLA and haploidentical marrow reduces graft-versus-host disease but it may impair a graft-versus-leukemia effect. Transpin. Proc. 19, 2701, 1987.

5. Sykes, M., Romick, M. L., Sachs, D. H. Interleukin 2 prevents graft-versus-host disease while preserving the graft-versus-leukemia effect of allogeneic T cells. *Proc. Nat. Acad. Sci.* 1990; 87: 5633.

6. Truitt, R. L., Atasoylu, A. A. Contribution of CD4+ and CD8+ T cells to graft-versus-host disease and the graft-versus-leukemia reactivity after transplantation of MHC compatible bone marrow *Bone Marrow Transplantation* 1991; 8:51.

7. Weiss, L., Lubin, I., Factorowich, I., Lapidot, Z., Reich, S., Reisner, Y., Slavin, S. Effective the graft-versus-leukemia effects independent of graft-versus-host disease after T cell depleted allogeneic bone marrow transplantation in a murine model of B cell leukemia/lymphoma. *J. Immunol.* 1994; 153: 2562.

8. Norton J, Al-Saffar N, Sloane J P. An immunohistological study of lymphocytes in human cutaneous graft-versus-host disease. *Bone Marrow Transplantation* 7:205, 1991.

9. Viale M, Ferrini S, Bacigalupo A. TCR positive lymphocytes after allogeneic bone marrow transplantation. *Bone Marrow Transplantation* 10:249, 1992.

10. Yabe M, Yabe H, Hattori K, Hinorhars T, Morimoto T, Kato S, Kusonoki A. Transition of T-cell receptor gamma/delta expressing double negative (CD4/CD8) lymphocytes after allogeneic bone marrow transplantation. *Bone Marrow Transplantation* 14:741,1994.

11. Tsuji S, Char D, Bucy R P, Simonsen M, Chen C, Cooper M D. +T-cells are secondary participants in acute graft-versus-host reactions initiated by CD4+ T-cells. *European Journal of Immunology* 26: 420, 1996.

12. Cela M E, Holliday M S, Rooney C M, Richardson S, Alexander B, Krance R A, Brenner M K, Heslop H E. +T-lymphocyte regeneration after T-lymphocyte-depleted bone marrow transplantation from mismatched family members or matched unrelated donors. *Bone Marrow Transplantation* 17:243, 1996.

13. Esslin A, Formby B. Comparison of cytolytic and proliferative activities of human and T-cells from peripheral blood against various human tumor cell lines. *Journal of the National Cancer Institute* 83:1564, 1994.

14. Orsini D L, VanGils M, Kooy Y M C, Struyk L, Klein G, van den Elsen P, Koning F. Functional and molecular characterization of B-cell-responsive V 1+ T-cells. *European Journal of Immunology* 24:3199, 1994.

15. Hoffman, T., Theobald, M., Bunjes, D., Weiss, M., Heimpel, H., Heidt, W. Frequency of bone marrow T cells responding to HLA-identical nonleukemic and leukemic stimulator cells. *Bone Marrow Transplantation* 1993; 12: 1.

16. Fisch, P., Malkovska, M., Braakman, E., Sturm, E., Bolhuis, R. L., Prieve, A., Sosman, J. A., Lam, V. A., Sondel, P. M. Gamma/delta T cell clones and natural killer cell clones mediate distinct patterns of non-major histocompatibility-restricted cytolysis. *J. Exp. Med.* 1990; 171: 1567.

17. Kaur, I., Voss, S. D., Gupta, R. S., Schell, K., Fisch, P., Sondel, P. M. Human peripheral gamma/delta T cells recognize hsp60 molecules on Daudi Burkitt's lymphoma cells. *J. Immunol.* 1993; 150: 2046.

18. Battistini, L., Salvetti, M., Falcone, B., Raine, C. S., Brosnan, C. F. Gamma delta T cell receptor analysis supports a role for HSP 70 selection of lymphocytes in multiple sclerosis lesions. *Mol. Med.* 1995; 1: 554.

19. Potential antileukemic effect of gamma delta T cells in acute lymphoblastic leukemia. *Leukemia* 1995: 9: 863.

20. Lamb L S, Henslee-Downey P J, Parrish R S, Godder K T, Thompson J, Lee C, Gee A P. Increased frequency of TCR- +T-cells in disease-free survivors following T-cell depleted partially mismatched bone marrow transplantation for leukemia. *Journal of Hematotherapy* 5:503, 1996.

21. Lamb, L. S., Gee, A., Hazlett, L, Musk, P., Parrish, R. S., O'Hanlon, T. P., Geier, S., Folk, R. S., Harris, W. G., McPherson, K., Lee, C., Henslee-Downey, P. J. Influence of T cell depletion method on circulating γδ+ T cell reconstitution and potential role in the graft-versus-leukemia effect Cytotherapy (in press).

22. Anasetti, C., Amos, D., Beatty, P G., Appelbaum, F. R. et al. Effect of HLA compatibility on engraftment of bone marrow transplants in patients with leukemia or lymphoma. *New Engl. J. Med.* 1989; 320: 197.

23. Anasetti, C., Beatty, P. G. Storb, R., Martin, P. J. et al. Effect of HLA incompatibility on graft-versus-host disease, relapse and survival after marrow transplantation for patients with leukemia or lymphoma. *Human Immunol.* 1990; 29: 79.

24. Beatty, P. G., Clift, R. A., Mickelson, E. M., Nisperos, B. B. Flournoy, N., Martin, P. J., Sanders, J. E., Stewart, P., Buckner, C. D., Storb, R., Thomas, E. D., Hansen, J. Marrow transplantation from related donors other than HLA-identical siblings. *New. Engl. J. Med.* 1985; 313: 765.

25. Gajewski., J., Ceka, M., Champlin, R. Bone marrow transplantation utilizing HLA-matched unrelated donors. *Blood Reviews* 1990; 4: 132.

26. Frame, J. N., Collins, N. H., Cartagena, T., Waldmann, H., O'Reilly, R., Dupont, B. & Kernan, N. A. T cell depletion of human bone marrow: comparison of Campath I plus complement, anti-T cell a-chain immunotoxin, and soybean agglutinin alone or in combination with sheep erythrocytes or immunomagnetic beads. *Transplantation,* 1989; 47: 984.

27. Kernan, N. A., Bordignon, C., Heller, G., Cunningham, I. et al. Graft failure after T cell depleted human leukocyte antigen identical marrow transplants for leukemia. *Blood* 1989; 74: 2227.

28. Martin, P. J., Hansen, J. A., Torok-Storb, B., Durnam, D. et al: Graft failure in patients receiving T cell depleted HLA-identical allogeneic marrow transplants. Bone Marrow Transplantation 1988; 3: 445.

29. Korngold, R. and Sprent, J. T cell subsets and graft-versus-host disease. Transpln Proc. 44, 335,1987.

30. Ash, R. C., Horowitz, M. M., Gale, R. P., van Bekkum, J. T. et al. Bone marrow transplantation from related donors other than HLA-identical siblings: effect of T cell depletion. Bone Marrow Transplantation 7, 441, 1991.

31. Henslee-Downey, P. J., Parrish, R., MacDonald, J. S., Romond, E. H., Marciniack, E., Coffey, C., Ciocci, G., Thompson, Jr. Combined in vitro and in vivo T lymphocyte depletion for the control of graft-versus-host disease following haploidentical marrow transplant. *Transplantation* 1886; 61; 738.

32. Lee, C., Henslee-Downey, P. J., Brouilette, M., Pati, A. R., Godder, K., Abhyankar, S. H., Gee, A. P. Comparison of OKT-3 and T10B9 for ex vivo T cell depletion of partially mismatched related donor bone marrow transplantation. *Blood* 1996; 86: 625a.

33. Goldman, J. M., Gale, R. P., Horowitz, M. M., Biggs, J. C., Champlin, R. E., Gluckman, E., Hoffman, R. G., Jacobsen, S. J., Marmot, A., M., McGlave, P. B., Messner, H. A., Rimm, A., A., Rozman, C., Speck, B., Tura, S., Weinger, R. S. & Bortin, M. M. Bone marrow transplantation for chronic myelogenous leukemia in chronic phase: Increased risk for relapse associated with T-cell depletion. *Ann Int Med,* 1988; 108; 806.

34. Hesner, M. J., Endean, D., Caspter, J. T., Horowitz, M. M., Keever-Taylor, C. A., Roth, M., Flomenberg, N., Drobyski, W. R. Use of unrelated marrow grafts compensates for reduced graft-versus-leukemia reactivity after T cell depleted allogeneic marrow transplantation for chronic myelogenous leukemia *Blood* 1995; 86: 3987.

35. Kolb, H. J., Schattenberg, A., Goldman, J. M., Hertenstein, B., Jacobsen, N., Arcese, W., Ljungman, P., Ferrant, A., Verdonck, L., Neiderweiser, D., van Rhee, F., Mittermueller, J., de Witte, T., Holler, E., Ansari, H. Graft-versus-leukemia effect of donor lymphocyte transfusions in marrow grafted patients. *Blood* 1995; 86: 2041.

36. Slavin, S., Naparstek, E., Nagler, A., Ackerstein, A., Kapelushnik, J., Or, R. Allogeneic cell therapy for relapsed leukemia after bone marrow transplantation with donor peripheral blood lymphocytes. *Exp. Hematol.* 1995; 23: 1553.

37. Antin, J. H. Graft-versus-leukemia: no longer an epiphenomenon. *Blood* 1993; 82: 2273.

38. Barrett, A. J. Strategies to enhance the graft-versus-malignancy effect in allogeneic transplants. *Ann NY Acad Sci* 1996; XX: 203.

39. Truitt, R. L., Johnson, B. D. Principles of graft-versus-leukemia reactivity. *Biol of Blood and Marrow Transplantation* 1995; 1: 61.

40. Datta, A. R., Barrett, A. J., Jiang, Y. Z., Guimaraes, A., Mavroudis, D. A., van Rhee, F., Gordon, A. A., Madrigal, A. Distinct T cell populations distinguish chronic myeloid leukemia cells from lymphocytes in the same individual: a model for separating GvHD from GVL reactions. *Bone Marrow Transplantation* 1994; 14: 517.

41. Champlin, R. Separation of graft-versus-host disease and graftversus-leukemia effect against chronic myelogenous leukemia. *Exp. Hematol.* 1995; 23: 1148.

42. Raulet, D. H. The structure, function, and molecular genetics of the γ/δ cell receptor. *Ann. Rev. Immunol.*, 1989; 7: 175.

43. Bigby, M., Markowitz, J. M., Bleicher, P. A., Grusby, M. J., Simha, S., Siebrecht, M., Wagner, M., Nagler-Anderson, C., Glimcher, L. H. most γδ T cells develop normally in the absence of MHC class II antigens. *J. Immunol.* 1993; 151: 4465.

44. Lanier, L. Unusual lymphocytes-γδ T cells and NK cells. *The Immunologist* 1995; 3; 182.

45. Schild, H., Mavaddat, N., Litzenberger, C., Ehrlich, E. W., Davis, M. M., Bluestone, J. A., Matis, L., Draper, R. K. Chien, y. The nature of major histocompatibility complex recognition by γδ+ T cells. *Cell* 1994; 76: 29.

46. Sperling, A. I., Linsley, P. S., Barrett, T. A., Bluestone, J. A. CD-28 mediated costimulation is necessary for the activation of T cell receptor-γδ+ T lymphocytes. *J. Immunol.* 1993; 151: 6043.

47. Wesselborg, S., Janssen, O., Pechhold, K., Kabelitz, D. Selective activation of γδ+ T cells by single anti-CD2 antibodies. J. Exp. Med. 1991; 173: 297.

48. Avdalovic, M., Fong, D., Formby, B. Adhesion and costimulation of proliferative responses of human γδ T cells by interaction of VLA-4 and VLA-5 with fibronectin. *Immunol Lett.* 1993; 35: 101.

49. Lin, T., Matsuzaki, G., Umesue, M., Omoto, K., Yoshida, H., Harada, M., Singaram, C., Hiromatsu, K., Nomoto, K. Development of γδ CD4-CD8+αα but not TCR-αβ CD4-CD8+αα i-IEL is resistant to cyclosporin A. *J. Immunol.* 1995; 155: 4224.

50. Ellison, C. A., MacDonald, G. C., Rector, E. S., Gartner, J. G. γδ T cells in the pathobiology of murine acute graft-versus-host disease. *J. Immunol.* 1995; 155: 4189.

51. Blazar, B. R., Taylor, P. A. Bluestone, J. A., Vallera, D. A. Murine γδ-expressing T cells affect alloengraftment via the reconognition of nonclassical major histocompatibility complex class Ib antigens. *Blood* 1996; 87: 4463.

52. Chouaib, F., Porto, P., Delorme, D., Hercend, T. Further evidence for a g/d T cell receptor-mediated TCT.1/CD48 recognition. *J. Immunol.* 147: 2864; 1991.

53. Hacker, G., Kromer, S., Falk, M., Heeg, K., Wagner, H., Pfeffer, K. Vδ1+ subset of human γδ T cells responds to ligands expressed by EBV-infected Burkitt lymphoma cells and transformed B lymphocytes. *J. Immunol.* 149: 3984; 1992.

54. Marx. S., Wesch, D., Kabelitz, D. Activation of humn γδ T cells by *Mycobacterium tuberculosis* and Daudi lymphoma cells. *J. Immunol.* 158: 2842; 1997.

55. Chomczynski P, Sacchi N. Single-step method of RNA isolation by guanidinium thiocyanate-phenol-chloroform extraction. *Anal. Biochem.* 1987; 162:156.

56. O'Hanlon, T. P., Messersmith, W., Dalakas, M. C., Plotz, P. H., and Miller, F. W. T Cell Receptor Gene Expression by Muscle-Infiltrating Lymphocytes in Idiopathic Inflammatory Myopathies. *Clin. Exp. Immunol.* 1995; 100: 519.

What is claimed is:

1. A method of treating a patient with acute lymphoblastic leukemia comprising the steps of:
    obtaining a donor material comprising bone marrow or peripheral blood collected from a donor;
    depleting said donor material in vitro of αβ+ T cells, thereby rendering the donor material rich in γδ+ T cells;
    activating said γδ+ T cells in vitro by treating said cells with a media comprising leukemia cells extracted from the patient and irradiated ex vivo, alone or in combination with an anti-T cell receptor (TCR) pan-δ antibody; and
    administering an effective amount of said activated γδ+ T cells to said leukemia patient, wherein said activated γδ+ T cells are cytolytic to the patient's leukemia cells but minimally cytotoxic to the patient's other cells.

2. The method in accordance with claim 1, wherein said donor material is enriched with γδ+ T cells by negative selection.

3. The method in accordance with claim 2, wherein said negative selection is performed using immunomagnetic microspheres associated with either CD4+ and CD8+ or an anti-TCRαβ monoclonal antibody.

4. The method in accordance with claim 1, wherein said activated γδ+ T cells predominantly express the Vδ1 phenotype.

5. The method in accordance with claim 1, wherein said activated γδ+ T cells predominantly express the Vδ2 phenotype.

6. The method in accordance with claim 1, wherein said donor material is enriched with γδ+ T cells by depleting the donor material of CD4+ and CD8+ T cells.

7. The method in accordance with claim 1, wherein said media consists essentially of irradiated leukemia blast cells extracted from said patient, an anti-TCR-pan-δ antibody, and interleukin-2.

8. The method in accordance with claim 1, wherein said activated γδ+ T cells are positive for CD3, CD25, and CD69 and negative for CD4 and CD8.

9. The method in accordance with claim 1, wherein said donor material is derived from an HLA-partially mismatched related donor.

10. The method in accordance with claim 1, wherein donor material is derived from an HLA-phenotypically matched unrelated donor.

* * * * *